(12) United States Patent
Liu et al.

(10) Patent No.: US 11,428,588 B2
(45) Date of Patent: Aug. 30, 2022

(54) FULLY-PASSIVE PRESSURE SENSORS AND METHODS FOR THEIR USE

(71) Applicant: Arizona Board of Regents on behalf of Arizona State University, Scottsdale, AZ (US)

(72) Inventors: Shiyi Liu, Tempe, AZ (US); Junseok Chae, Scottsdale, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 296 days.

(21) Appl. No.: 16/834,726

(22) Filed: Mar. 30, 2020

(65) Prior Publication Data
US 2020/0309612 A1 Oct. 1, 2020

Related U.S. Application Data
(60) Provisional application No. 62/825,132, filed on Mar. 28, 2019.

(51) Int. Cl.
| | | |
|---|---|---|
| *G01L 9/00* | (2006.01) | |
| *A61B 5/03* | (2006.01) | |
| *G01L 1/08* | (2006.01) | |
| *A61B 5/00* | (2006.01) | |

(52) U.S. Cl.
CPC ............ *G01L 1/086* (2013.01); *G01L 9/0002* (2013.01); *A61B 5/0048* (2013.01); *A61B 5/031* (2013.01); *A61B 5/032* (2013.01); *G01L 2009/0066* (2013.01); *G01L 2009/0069* (2013.01)

(58) Field of Classification Search
CPC ..... G01L 2009/0069; G01L 2009/0066; G01L 9/0002; A61B 5/032; A61B 5/031
See application file for complete search history.

(56) References Cited

U.S. PATENT DOCUMENTS

| | | |
|---|---|---|
| 4,033,357 A | 7/1977 | Helland et al. |
| 4,041,954 A | 8/1977 | Ohara |
| 6,790,178 B1 | 9/2004 | Mault et al. |
| 6,871,084 B1 | 3/2005 | Kingsley et al. |
| 6,889,086 B2 | 5/2005 | Mass et al. |
| 8,019,419 B1 | 8/2011 | Panescu et al. |

(Continued)

FOREIGN PATENT DOCUMENTS

| | | |
|---|---|---|
| WO | 2009064577 A1 | 5/2009 |
| WO | 2010088219 A2 | 8/2010 |

(Continued)

OTHER PUBLICATIONS

Abbaspour-Tamijani et al., "A miniature fully-passive microwave back-scattering device for short-range telemetry of neural potentials", 30th Annual International Conference of the IEEE Engineering in Medicine and Biology Society {Vancouver, British Columbia, Canada, Aug. 20-24, 2008), pp. 129-132 <DOI:10.1109/IEMBS. 2008.4649107>.

(Continued)

*Primary Examiner* — Paul M. West
(74) *Attorney, Agent, or Firm* — Riverside Law LLP

(57) ABSTRACT

Fully-passive sensor systems that receive an input electromagnetic signal and return an output electromagnetic signal are described. The sensor systems can be used to measure pressure in biological or non-biological systems.

17 Claims, 4 Drawing Sheets

(56) References Cited

U.S. PATENT DOCUMENTS

| | | | |
|---|---|---|---|
| 8,129,622 | B2 | 3/2012 | Taylor et al. |
| 8,321,021 | B2 | 11/2012 | Kisker et al. |
| 8,345,910 | B2 | 1/2013 | Chae et al. |
| 8,725,270 | B2 | 5/2014 | Towe |
| 8,909,343 | B2 | 12/2014 | Towe |
| 8,923,963 | B2 | 12/2014 | Bonner et al. |
| 9,168,383 | B2 | 10/2015 | Jacobson et al. |
| 9,358,136 | B2 | 6/2016 | Stein et al. |
| 9,409,029 | B2 | 8/2016 | Perryman et al. |
| 9,446,255 | B2 | 11/2016 | Towe et al. |
| 9,623,253 | B2 | 4/2017 | Perryman et al. |
| 9,693,708 | B2 | 7/2017 | Towe |
| 9,700,712 | B2 | 7/2017 | Towe |
| 9,935,498 | B2 | 4/2018 | Joshi |
| 10,119,960 | B2 | 11/2018 | Chae et al. |
| 10,576,305 | B2 | 3/2020 | Maharbiz et al. |
| 11,000,257 | B2 | 5/2021 | Adler et al. |
| 2006/0020224 | A1 | 1/2006 | Geiger |
| 2006/0235484 | A1 | 10/2006 | Jaax et al. |
| 2007/0089525 | A1* | 4/2007 | Momose ............... G01L 9/0025 73/753 |
| 2008/0183247 | A1 | 7/2008 | Harding |
| 2008/0275356 | A1 | 11/2008 | Stasz et al. |
| 2009/0204170 | A1 | 8/2009 | Hastings et al. |
| 2009/0299216 | A1 | 12/2009 | Chen et al. |
| 2010/0016762 | A1 | 1/2010 | Thapliyal et al. |
| 2010/0198039 | A1 | 8/2010 | Towe |
| 2010/0324378 | A1 | 12/2010 | Tran et al. |
| 2011/0004076 | A1 | 1/2011 | Janna et al. |
| 2013/0018440 | A1 | 1/2013 | Chow et al. |
| 2013/0261703 | A1 | 10/2013 | Chow et al. |
| 2014/0276048 | A1 | 9/2014 | Kiley et al. |
| 2014/0350348 | A1 | 11/2014 | Tee et al. |
| 2015/0265171 | A1* | 9/2015 | Seaver ................. A61B 5/6852 600/561 |
| 2016/0017268 | A1 | 1/2016 | Kim et al. |
| 2016/0030757 | A1 | 2/2016 | Jacobson |
| 2016/0367186 | A1 | 12/2016 | Freeman et al. |
| 2017/0095198 | A1 | 4/2017 | Towe |
| 2017/0209094 | A1 | 7/2017 | Derchak et al. |
| 2018/0192941 | A1 | 7/2018 | Annoni et al. |
| 2018/0358119 | A1 | 12/2018 | Bhushan et al. |
| 2019/0021692 | A1 | 1/2019 | Utsugida et al. |
| 2019/0223782 | A1 | 7/2019 | Wen et al. |
| 2019/0229770 | A1 | 7/2019 | Khaleghi et al. |
| 2019/0254565 | A1 | 8/2019 | Toth et al. |
| 2019/0343410 | A1* | 11/2019 | Bahmanyar .......... A61B 5/0215 |
| 2020/0001089 | A1 | 1/2020 | Chae |
| 2020/0253578 | A1 | 8/2020 | Chae et al. |
| 2020/0289002 | A1 | 9/2020 | Chae et al. |
| 2021/0052225 | A1 | 2/2021 | Shetty et al. |

FOREIGN PATENT DOCUMENTS

| | | | |
|---|---|---|---|
| WO | 2014144219 | A1 | 9/2014 |
| WO | 2015191600 | A1 | 12/2015 |
| WO | 2018011235 | A1 | 1/2018 |

OTHER PUBLICATIONS

Arfin, S. et al., "Wireless Neural Stimulation in Freely Behaving Small Animals", Journal of Neurophysiology, Jul. 2009 [available online Apr. 2009], vol. 102, No. 1, pp. 598-605 <DOI:10.1152/jn. 00017.2009>.

Auricchio, First-in-man implantation of leadless ultrasound-based cardiac stimulation pacing system: novel endocardial left ventricular resynchronization therapy in heart failure patients, Europace, p. 1191-1197, 2013.

Auricchio, "Feasibility, safety, and short-term outcome of leadless ultrasound-based endocardial left ventricular resynchronization in heart failure patients: results of the Wireless Stimulation Endocardially for CRT (WiSE-CRT) study," Europace, p. 681-688, 2014.

Berger et al., Brain mapping techniques to maximize resection, safety, and seizure control in children with Brain tumors, Neurosurgery, Nov. 1989, pp. 786-792, vol. 25 issue 5.

Berger et al., Intraoperative brain mapping techniques in neuro-oncology, Stereotactic and Functional Neurosurgery, 1992, pp. 153-161, vol. 58.

Bers, D., "Calcium Fluxes Involved in Control of Cardiac Myocyte Contraction", Circulation Research, Aug. 2000, vol. 87, pp. 275-281 <DOI:10.1161/01.RES.87.4275>.

Blumcke et al., Histopathological Finding in Brain Tissue Obtained during Epilepsy Surgery, New England Journal of Medicine, 2017, pp. 1648-1656, vol. 377.

Chen, A. et al., "Low-voltage shock mitigated micro-electromechanical systems structure", Applied Physics Letters, May 2017, vol. 110, No. 20, pp. 201903-1-5 <DOI: 0.1063/1.4983645>.

Chow, E. et al., "Implantable RF Medical Devices: The Benefits of High-Speed Communication and Much Greater Communication Distances in Biomedical Applications", IEEE Microwave Magazine, Jun. 2013, vol. 14, No. 4, pp. 64-73 <DOI:10.1109/MMM.2013.2248586>.

Davis, New Fibre Optic Sensor for Respiratory Monitoring, Engineering Information Abstracts (Part II), p. 122-123.

Davis et al., A new sensor for monitoring chest wall motion during high-frequency oscillatory ventilation, Medical Engineering and Physics, 1999, pp. 619-623, vol. 21.

De Cock, C.C., Comparison of the haemodynamic effects of right ventricular outflow-tract pacing with right ventricular apex pacing, Europace, p. 275-278, Jul. 2003.

De Venuto, D. et al., "RFID transceiver for wireless powering brain implanted microelectrodes and backscattered neural data collection", Microelectronics Journal, Dec. 2014 [available online Sep. 2014], vol. 45, No. 12, pp. 1585-1594 <DOI:10.1016/J.MEJO.2014.08.007>.

Eseonu et al., Awake Craniotomy vs Craniotomy Under General Anesthesia for Perirolandic Gliomas: Evaluating Perioperative Complications and Extent of Resection, Neurosurgery, Sep. 2017, pp. 481-489, vol. 81 Issue 3.

Feyissa et al., High-frequency oscillations in awake patients undergoing brain tumor-related epilepsy surgery, Neurology, Mar. 2018, pp. e1119-e1125, vol. 90.

Folke et al., Critical review of non-invasive respiratory monitoring in medical care, Medical and Biological Engineering and Computing, 2003, pp. 377-383, vol. 41.

Formaggio et al., Frequency and lime-frequency analysis of intraoperative ECoG during awake brain stimulation, Frontiers in Neuroengineering, 2013, vol. 6.

Franks et al., Contactless respiration monitoring of infants, Medical and Biological Engineering, May 1976, pp. 306-312.

Fregni, F. et al., "A sham-controlled, phase II trial of transcranial direct current stimulation for the treatment of central pain in traumatic spinal cord injury", Pain, May 2006 [available online Mar. 2006], vol. 122, No. 1, pp. 197-209 <DOI:10.1016/j.pain.2006.02.023>.

Graham, Emmelyn M., Quantitative mapping of aqueous microfluidic temperature with sub-degree resolution using fluorescence lifetime imaging microscopy, Lab on a Chip, p. 1267-1273, 2010.

Guy, Arthur W., Analyses of Electromagnetic Fields Induced in Biological Tissues by Thermographic Studies on Equivalent Phantom Models, IEEE Transactions on Microwave Theory and Techniques, p. 205-214, Feb. 1971.

Harrison, R., "Designing Efficient Inductive Power Links for Implantable Devices", 2007 IEEE International Symposium on Circuits and Systems (New Orleans, Louisiana, Jun. 2007), pp. 2080-2083 <DOI: 10.1109/ISCAS.2007 .378508>.

Hirt, M. et al., "Functional improvement and maturation of rat and human engineered heart tissue by chronic electrical stimulation", Journal of Molecular and Cellular Cardiology, Sep. 2014 [available online May 2014], vol. 74, pp. 151-161 <DOI:10.1016/j.yjmcc.2014.05.009>.

Hossmann, K.A., Effects of Electromagnetic Radiation of Mobile Phones on the Central Nervous System, Bioelectromagnetics, p. 49-62, 2003.

(56) References Cited

OTHER PUBLICATIONS

Ito, Development and Characteristics of a Biological Tissue-Equivalent Phantom for Microwaves, Electronics and Communications in Japan, p. 67-77, 2001.
Kampianakis, E. et al., "A dual-band wireless power transfer and backscatter communication approach for implantable neuroprosthetic devices", 2017 IEEE International Conference on RFID (Phoenix, Arizona, May 9-11, 2017), Jun. 2017, pp. 67-72 <DOI:10.1109/RFID.2017.7945589>.
Knops, Chronic Performance of a Leadless Cardiac Pacemaker, Journal of the American College of Cardiology, p. 1497-1504, Apr. 21, 2015.
Kwan et al., Definition of drug resistant epilepsy: consensus proposal by the ad hoc Task Force of the ILAE Commission on Therapeutic Strategies, Epilepsia, Jun. 2010, pp. 1069-1077, vol. 51 issue 6.
Kwan et al., Early identification of refractory epilepsy, New England Journal of Medicine, Feb. 2000, pp. 314-319, vol. 342 issue 5.
Kwan et al., Erratum-Definition of drug resistant epilepsy: consensus proposal by the ad hoc Task Force of the LAE Commission on Therapeutic Strategies, Epilepsia, Sep. 2010, pp. 1922, vol. 51 issue 9.
Larson, P. et al., "Miniature ultrasonically powered wireless nerve cuff stimulator", 2011 5th International IEEE/EMBS Conference on Neural Engineering (Cancun, Mexico, Apr. 27-May 1, 2011), pp. 265-268 <DOI:10.1109/NER.2011.5910538>.
Leclercq, C., Comparative effects of permanent biventricular and right-univentricular pacing in heart failure patients with chronic atrial fibrillation, European Heart Journal, p. 1780-1787, Nov. 2002.
Lee, E. et al., "A Biomedical Implantable FES Battery-Powered Micro-Stimulator", IEEE Transactions on Circuits and Systems-I: Regular Papers, Oct. 2009 [IEEE Date of Publication: Dec. 2009], vol. 56, No. 12, pp. 2583-2596 <DOI:10.1109/TCSI.2009.2034052>.
Lee, S. et al., "A Low-Power Bidirectional Telemetry Device With a Near-Field Charging Feature for a Cardiac Microstimulator", IEEE Transactions on Biomedical Circuits and Systems, Apr. 2011 [IEEE Date of Publication: Aug. 2011], vol. 5, No. 4, pp. 357-367 <DOI:10.1109/TBCAS.2011.2126570>.
Lee, H. et al., "A Power-Efficient Wireless System With Adaptive Supply Control for Deep Brain Stimulation", IEEE Journal of Solid-State Circuits, Sep. 2013, vol. 48, No. 9, pp. 2203-2216 <DOI:10.1109/JSSC.2013.2266862>.
Liu, Shiyi, Wireless Passive Stimulation of Engineered Cardiac Tissues, ACS Sensors, p. 1006-12, 2017.
Marks et al., Aminoff's Electrodiagnosis in Clinical Neurology (6th Edition), L. Saunders Ed., Chapter 7—Invasive Clinical Neurophysiology in Epilepsy and Movement Disorders, 2012.
McDermott, H., "An advanced multiple channel cochlear implant", IEEE Transactions on Bio-medical Engineering, Jul. 1989, vol. 36, No. 7, pp. 789-797 <DOI:10.1109/10.32112>.
Means, David L., Evaluating Compliance with FCC Guidelines for Human Exposure to Radiofrequency Electromagnetic Fields, FCC Office of Technology Bulletin 65, Supplement C, p. 1-53, Jun. 2001.
Migrino, Raymond Q., Assessment of Segmental Myocardial Viability Using Regional 2-dimensional Strain Echocardiography, Journal of the American Society of Echocardiography, p. 342-351, Apr. 2007.
Miller et al., Standardisation of sprirometry, European Respiratory Journal, 2005, pp. 319-338, vol. 26 No. 2.
Nakajima et al., Monitoring of heart and respiratory rates by photoplethysmography using a digital filtering technique, Medical Engineering and Physics, 1996, pp. 365-372, vol. 18 No. 5.
Navaei, Ali, Electrically conductive hydrogel-based microtopographies for the development of organized cardiac issues, Royal Society of Chemistry Advances, p. 3302-3312, 2017.
Navaei, Ali, Gold nanorod-incorporated gelatin-based conductive hydrogels for engineering cardiac tissue constructs, Acta Biomaterialia, p. 133-146, May 2016.
Navaei, A. et al., "PNIPAAm-based biohybrid injectable hydrogel for cardiac tissue engineering", Acta Biomaterialia, Mar. 2016 [available online Dec. 2015], vol. 32, pp. 10-23 <DOI:10.1016/j.actbio.2015.12.019>.
Nilsson et al., Monitoring of Respiratory Rate in Postoperative Care Using a New Photoplethysmographic technique, Journal of Clinical Monitoring and Computing, 2000, pp. 309-315, vol. 16 No. 4.
Niosh Spirometry Training Guide, Dec. 1, 2003, pp. 1-257, Universities Occupational Safety and Health Educational Resource Center and Centers for Disease Control and Prevention National Institute for Occupational Safety and Health.
Obeid, D. et al., "Low power microwave systems for heartbeat rate detection at 2.4, 5.8, 10 and 16 GHz", 2008 First International Symposium on Applied Sciences on Biomedical and Communication Technologies {Aalborg, Denmark, Oct. 25-28, 2008; pp. 1-5 <DOI:10.1109/ISABEL.2008.4712623>.
Okano, Yoshinobu, The SAR Evaluation Method by a Combination of Thermographic Experiments and Biological Tissue-Equivalent Phantoms, IEEE Transactions on Microwave Theory and Techniques, p. 2094-2103, Nov. 2000.
Ovadia, Marc, The Electrode-Tissue Interface in Living Heart: Equivalent Circuit as a Function of Surface Area, Electroanalysis, p. 262-272, 1998.
Peckham, P. et al., "Functional Electrical Stimulation for Neuromuscular Applications", Annual Review of Biomedical Engineering, Aug. 2005 [available online Mar. 2005], vol. 7, pp. 327-360 <DOI:10.1146/annurev.bioeng.6.040803.140103>.
Pfurtscheller, G. et al., "'Thought'-control of functional electrical stimulation to restore hand grasp in a patient with tetraplegia", Neuroscience Letters, Nov. 2003, vol. 351, pp. 33-36 <DOI:10.1016/s0304-3940{03)00947-9>.
Piezo Film Sensors Technical Manual, Apr. 1999, pp. 1-89, Measurement Specialties, Inc.
Prinzen, Frits W., Relation Between the Pacing Induced Sequence of Activation and Left Ventricular Pump Function in Animals, Journal of Pacing and Clinical Electrophysiology, p. 484-98, Apr. 2002.
Radioactive Consumer Products, Glossy Paper, www.orau.org/PTP/collection/consumer/o20products/magazines.htm <http://www.orau.org/PTP/collection/consumer%22/o20products/magazines.htm>, 2009, pp. 1-2.
Reddy, Vivek, Cardiac Resynchronization Therapy with Wireless Left Ventricular Endocardial Pacing, Journal of the American College of Cardiology, p. 2119-2129, May 2, 2017.
Ren, H. et al., "Improved current and power density with a micro-scale microbial fuel cell due to a small characteristic length", Biosensors and Bioelectronics, Nov. 2014 [available online Jun. 2014], vol. 61, pp. 587-592 <DOl: 10.1016/j.bios.2014.05.037>.
Schulman, J., "The Feasible FES System: Battery Powered BION Stimulator", Proceedings of the IEEE, Jul. 2008, vol. 96, No. 7, pp. 1226-1239 <DOI:10.1109/JPROC.2008.922588>.
Schwan, H. et al., "The Conductivity of Living Tissues", Annals of the New York Academy of Sciences, Aug. 1957, vol. 65, No. 6, pp. 1007-1013 <DOI:10.1111/j.1749-632.1957.tb36701 .x>.
Schwerdt, Helen N., Analysis of Electromagnetic Fields Induced in Operation of a Wireless Fully Passive Backscattering Neurorecording Microsystem in Emulated Human Head Tissue, IEEE Transactions on Microwave Theory and Techniques, p. 2170-2176, May 2013.
Schwerdt, Helen N., A fully Passive Wireless Backscattering Neurorecording Microsystem Embedded in Dispersive Human-Head Phantom Medium, IEEE Electron Device Letters, p. 908-910, Jun. 2012.
Schwerdt, Helen N., A Fully Passive Wireless Microsystem for Recording of Neuropotentials Using RF Backscattering Methods, Journal of Microelectromechanical Systems, p. 1119-1130, Oct. 2011.
Schwerdt, H. et al., "Preliminary thermal characterization of a fully-passive wireless backscattering neuro-recording microsystem", 2011 16th International Solid-State Sensors, IEEE Actuators and Microsystems Conference {Beijing, China, Jun. 5-9, 2011), [Date Added to IEEE Xplore: Aug. 2011], pp. 1228-1231 <DOI:10.1109/TRANSDUCERS.2011.5969400>.

(56) References Cited

OTHER PUBLICATIONS

Se Dong Min et al., A study on a non-contacting respiration signal monitoring system using Doppler ultrasound, Medical and Biological Engineering and Computing, Nov. 2007, pp. 1113-1119, vol. 45 issue 11.
Seif-Naraghi, Sonya B., Safety and Efficacy of an Injectable Extracellular Matrix Hydrogel for Treating Myocardial Infarction, Science Translational Medicine, p. 1-10, Feb. 20, 2013.
Semmes et al., Subjective and Objective Measurement of Tidal Volume in Critically Ill Patients, Chest Journal, May 1985, pp. 577-579, vol. 87 issue 5, Official Publication of the American College of Chest Physicians.
Shimada, Y. et al., "Clinical use of percutaneous intramuscular electrodes for functional electrical stimulation", Archives of Physical Medicine and Rehabilitation, Oct. 1996, vol. 77, No. 10, pp. 1014-1018 <DOI:10.1016/s0003-9993(96)90061-1 >.
Siew-Mooi Ching et al., Detection of airflow limitation using a handheld spirometer in a primary care selling, Respirology, Apr. 7, 2014, pp. 689-693, vol. 19.
Simmons, Inside Laser Printer Toner: Wax, Static, Lois of Plastic, Mar. 23, 2015, www.wired.com/2015/03/hals-inside-prinler-loner/.
Smith, B. et al., "An Externally Powered, Multichannel, Implantable Stimulator for Versatile Control of Paralyzed Muscle", IEEE Transactions on Bio-medical Engineering, Jul. 1987, vol. BME-34, No. 7, pp. 499-508 <DOI:10.1109/tbme.1987 .325979>.
Sun, Y. et al., Wirelessly powered implantable pacemaker with on-chip antenna, 2017 IEEE MTT-S International Microwave Symposium {Honolulu, Hawaii, Jun. 4-9, 2017), [IEEE Date of Publication: Oct. 2017], pp. 1242-1244 <DOI:10.1109/MWSYM.2017. 8058831>.
Sweeney, Michael 0., A New Paradigm for Physiologic Ventricular Pacing, Journal of the American College of Cardiology, p. 282-288, Jan. 17, 2006.
Takahashi, A. et al., "Measurement of intracellular calcium", Physiological Reviews, Oct. 1999 [available online Jan. 1999], vol. 79, No. 4, pp. 1089-1125 <DOI:10.1152/physrev.1999.79.4.1089>.
Tandon, N. et al., "Electrical stimulation systems for cardiac tissue engineering", Nature Protocols, Jan. 2009, vol. 4, No. 2, pp. 155-173 <DOI:10.1038/nprot.2008.183>.
Tandon, N. et al., "Optimization of electrical stimulation parameters for cardiac tissue engineering", Journal of Tissue Engineering and Regenerative Medicine, Jun. 2011 [available online Jan. 2011], vol. 5, No. 6, pp. e115-e125 <DOI:10.1002/term.377>.
Voorhies et al., Techniques for placement of grid and strip electrodes for intracranial epilepsy surgery monitoring: Pearls and pitfalls, Surgical Neurology International, 2013, vol. 4.
Wade, Movements of the Thoracic Cage and Diaphragm in Respiration, The Journal of Physiology, May 28, 1952, pp. 183-212, vol. 124 No. 2.
Walter, P. et al., "Cortical activation via an implanted wireless retinal prosthesis", Investigate Ophthalmology and Visual Science, May 2005, vol. 46, No. 5, pp. 1780-1785 <DOI:10.1167/iovs.04-0924>.
Wang, Jianqing, FDTD calculation of whole-body average SAR in adult and child models for frequencies from 30MHz to 3 GHz, Physics in Medicine and Biology, p. 4119-4127, 2006.
Want, R., "An introduction to RFID technology", IEEE Pervasive Computing, Jan. 2006, vol. 5, No. 1,pp. 25-33 <DOI:10.1109/MPRV. 2006.2>.
Wehrle et al., A fibre optic Bragg grating strain sensor for monitoring ventilatory movements, Measurement Science and Technology, 2001, pp. 805-809, vol. 12 No. 7.
Wolf, P., "Thermal Considerations for the Design of an Implanted Cortical Brain-Machine Interface", In: Reichert, W. M. {Ed.), "Indwelling Neural Implants: Strategies for Contending with the In Vivo Environment", CRC Press/Taylor & Francis, 2008, Chapter 3.
Wyler et al., Subdural strip electrodes for localizing epileptogenic foci, Journal of Neurosurgery, 1984, pp. 1195-1200, vol. 60.
Yamamoto, J. et al., "Low-frequency Electric Cortical Stimulation Has an Inhibitory Effect on Epileptic Focus in Mesial Temporal Lobe Epilepsy", Epilepsia, May 2002, vol. 43, No. 5, pp. 491-495 <DOI:10.1046/.1528-1157.2002.29001.x>.
Yu, Yinghong, Biventricular mechanical asynchrony predicts hemodynamic effect of uni- and biventricular pacing, AJP Heart Circ Physiol, p. H2788-2796, Dec. 2003.
Zealear, D. et al., "The biocompatibility, integrity, and positional stability of an injectable microstimulator for reanimation of the paralyzed larynx", IEEE Transactions on Bio-medical Engineering, Aug. 2001, vol. 48, No. 8, pp. 890-897 <DOI:10.1109/10.936365>.
Zehendner, Christoph, A Simple and Novel Method to Monitor Breathing and Heart Rate in Awake and Urethane-Anesthetized Newborn Rodents, PLOS One, p. 1-9, May 2013.
Zhang, X. et al., "Working Distance Comparison of Inductive and Electromagnetic Couplings for Wireless and Passive Underwater Monitoring System of Rinsing Process in Semiconductor Facilities", IEEE Sensors Journal, May 2011 [IEEE Dale of Publication: Nov. 2011], vol. 11, No. 11, pp. 2932-2939 <DOI:10.1109/JSEN. 2011.2151185>.
Ziaie, B. et al., "A single-channel implantable microstimulator for functional neuromuscular stimulation", IEEE Transactions on Bio-medical Engineering, Oct. 1997, vol. 44, No. 10, pp. 909-920 <DOI:10.1109/10.634643>.
Bashirullah, Wireless Implants, IEEE Microwave Magazine, Dec. 2010, pp. S14-S23, vol. 11, issue No. 7.
Chen, A. et al., "Wireless Wearable Ultrasound Sensor on a Paper Substrate to Characterize Respiratory Behavior", ACS Sensors, Mar. 2019, vol. 4, No. 4, pp. 944-952 <DOI:10.1021/acssensors. 9b00043>.
Cop, W., "Methods and Devices Used in Ventilatory Monitoring", Encyclopedia of Medical Devices and Instrumentation, 1988, vol. 4, pp. 2870-2877.
Guder, F. et al., "Paper-Based Electrical Respiration Sensor", Angewandte Chemie International Edition, May 2016 [available online Apr. 2016], vol. 55, No. 19, pp. 5727-5732 <DOI:10.1002/ anie.201511805>.
Guin, P. et al., "Design of efficient loadcell for measurement of mechanical impact by piezoelectric PVDF film sensor", AIP Advances, Sep. 2016, vol. 6, No. 9, article No. 095122, 5 pages <DOI:10. 1063/1.4964148>.
Harris. G. et al., "The impact of piezoelectric PVDF on medical ultrasound exposure measurements, standards, and regulations", IEEE transactions on ultrasonics, ferroelectrics, and frequency control, Nov. 2000, vol. 47, No. 6, pp. 1321-1335 <DOI:10.1109/ 58.883521 >.
Jow et al., Design and Optimization of Printed Spiral Coils for Efficient Transcutaneous Inductive Power Transmission, IEEE Transactions on Biomedical Circuitsand Systems, Sep. 2007, pp. 193-202, vol. 1, issue No. 3.
Magori, V. et al., "Ultrasonic sensors in air", Ultrasonics Symposium (Oct. 31-Nov. 3, 1994), 1994, vol. 1, pp. 471-481.
O'Reilly, M. et al., "A PVDF receiver for ultrasound monitoring of transcranial focused ultrasound therapy", IEEE Transactions on Biomedical Engineering, Sep. 2010 [IEEE date of publication: May 2010], vol. 57, No. 9, pp. 2286-2294 <DOI: 10.1109/TBME.2010. 2050483>.
Raboel et al., Intracranial Pressure Monitoring: Invasive versus Non-Invasive Methods—A Review, Critical Care Research and Practice; vol. 2012 Article ID 950393, Accepted Mar. 27, 2012.
Ramrakhyani et al., Design and Optimization of Resonance-Based Efficient Wireless Power Delivery Systems for Biomedical Implants, IEEE Transactions on Biomedical Circuits and Systems, Feb. 2011 [IEEE publication date: Oct. 2010], pp. 48-63, vol. 5, issue No. 1.
Ramrakhyani et al., On the Design of Efficient Multi-Coil Telemetry System for Biomedical Implants, IEEE Transactions on Biomedical Circuits and Systems, Feb. 2013 [IEEE publication date Apr. 2012], pp. 11-23, vol. 7, issue No. 1.
Seo, M. et al., "A simple breathing rate-sensing method exploiting a temporarily condensed water layer formed on an oxidized surface", Applied Physics Letters, Feb. 2015, vol. 106, No. 5, article No. 053701, 4 pages <DOI:10.1063/1.4906815>.
Wansch, Small antennas for wireless micro-systems, Active and Passive Electronic Components, 2002, pp. 71-82, vol. 25.

(56) References Cited

OTHER PUBLICATIONS

Yu, Y. et al., "Wrinkled nitrile rubber films for stretchable and ultra-sensitive respiration sensors", Extreme Mechanics Letters, Feb. 2017 [available online Dec. 2016], vol. 11, pp. 128-136 <DOI:10.1016/j.eml.2016.12.003>.

Zhang, X., et al., A wireless and passive wafer cleanliness monitoring unit via electromagnetic coupling for semicondutcor/MEMS manufacturing facilities, Sensors and Actuators A: Physical, Nov. 2011, pp. 414-420, vol. 171, issue No. 2.

\* cited by examiner

FULLY-PASSIVE PRESSURE SENSORS AND METHODS FOR THEIR USE

CROSS-REFERENCE TO RELATED APPLICATIONS

This application claims priority to U.S. Provisional Patent Application Ser. No. 62/825,132, which was filed on Mar. 28, 2019, is entitled Subcutaneous Passive Wireless Pressure Sensors, and which is incorporated by reference in its entirety into this application.

GOVERNMENT LICENSE RIGHTS

This invention was made with government support under 1734806 awarded by the National Science Foundation. The government has certain rights in the invention.

TECHNICAL FIELD

This application relates generally to electromagnetic wave sensors. In particular, this application relates to systems and devices comprising a pressure sensor. Example uses include using the sensors to measure pressure within a patient or other biological system.

TECHNICAL BACKGROUND

The use of RF (radio frequency) technology in biomedical applications has been largely limited due to the highly adsorptive nature of RF wave in aqueous materials, and the resulting potential harm to the brain or other target location. This fundamental challenge or concern serves to dissuade the use of RF to power any device implanted inside the brain. RF coupling faces severe challenges when an implant requires powering electronics: ultra-low efficiency and safety uncertainties, such as unwanted temperature rise within tissues, associated with the wireless power transfer. When RF travels in dissipative media, including aqueous media such as tissue, the power of RF decreases significantly, for example by 3-5 dB/cm, which can result in an unwanted temperature rise. Such temperature rise becomes especially critical inside the skull as neurons are very sensitive to temperature change. Written reports have provided that changes of plus or minus 1 degree Celsius may cause neurons to function abnormally, and changes of plus or minus 5 degrees Celsius result in neuron damage.

There exists a need for technologies to encourage the use of RF in various systems.

DETAILED DESCRIPTION

Figure 1:
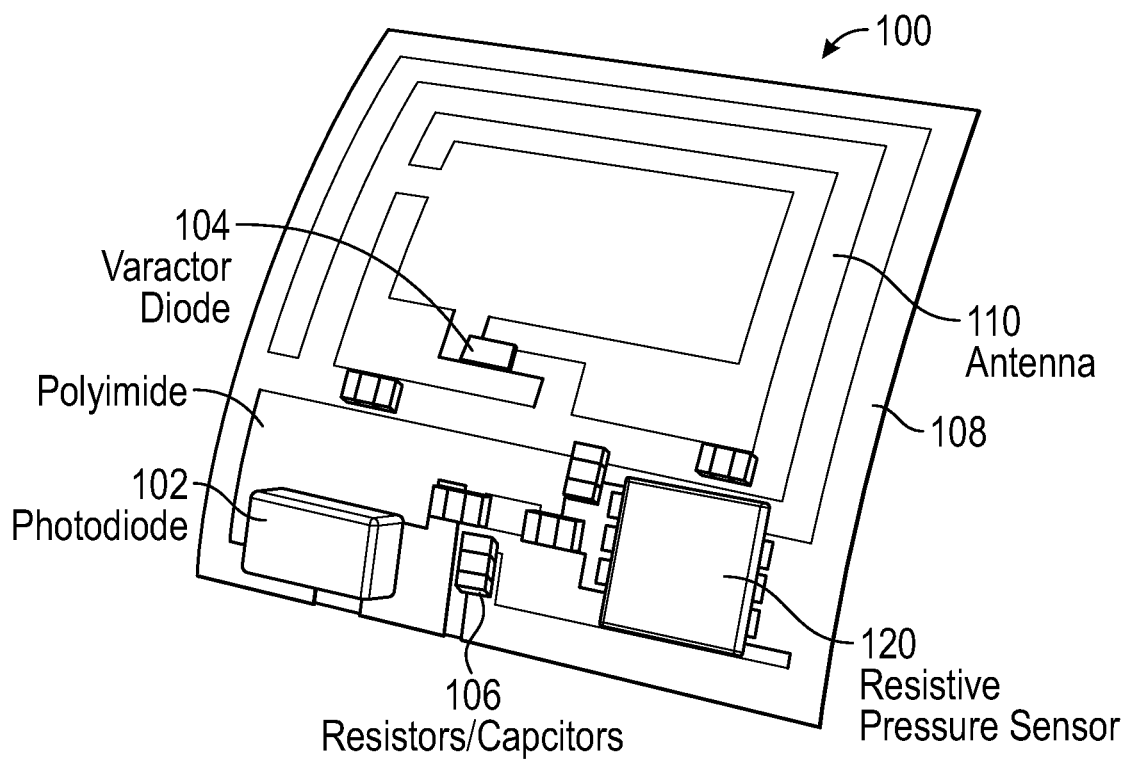
FIG. 1 illustrates a fully-passive sensor system as may be employed in embodiments.

Systems, devices, and methods involving a fully-passive sensor system or surface-mounted sensor system that receives electromagnetic signals from an external source and returns one or more electromagnetic signals are described herein. The returned signals may be used to determine pressure being applied to the fully-passive sensor system.

As used herein, "fully-passive" refers to a component or system that does not contain a battery or other formal power source. In contrast, a "passive" component or system does not contain a battery, but does receive power from an external battery or power source. In other words, fully-passive devices do not themselves include any electronics on board that consume power. With a fully-passive device, for example, an electromagnetic wave may be sent to the device; instead of powering the device, the wave causes electromagnetic backscattering, and an external detector can then recover the signal.

The fully-passive sensor system of various embodiments may measure the pressure of its surroundings without any external connections, which may provide the advantage of achieving an implantation fully concealed within the cranium or other subcutaneous target area. In some embodiments, the measurable pressure range of the sensor may be limited within positive pressure due to the unipolarity of the pressure sensing mechanism. In some embodiments, one-way pressure sensing may be related to the geometry of a sensor and its use of deformable metal electrodes and a conductive sheet. Contact between the electrodes and conductive sheet leading to electric signal change may be seen in positive pressure ranges, may be read, and may be determined in some embodiments. Some embodiments may incorporate two or more sensors for pressure measurement in opposing or orthogonal or otherwise related directions. Some embodiments may provide a single sensor with bipolarity for bi-directional pressure sensing.

Some embodiments may employ the reflection of microwave with a RF backscattering effect to acquire inter-cranial pressure (ICP), or other measurements, without using a battery to power the fully-passive sensor system. Some embodiments may, therefore, provide for a unique wireless fully-passive biotelemetry of ICP, using the RF backscattering effect, on a miniaturized platform which can integrate zero-power consuming electronics utilizing Micro-Electro-Mechanical-Systems (MEMS) technology. Unlike inductive coupling, some embodiments may employ small antennas to provide an RF link to and between implants, whether positioned subcutaneously, outside of the skin, or both.

Side-by-side comparisons of inductive and RF couplings have demonstrated unique advantages of RF coupling. Analysis shows that RF experiences more attenuation through tissue. As such, an increase in frequency results in an increase in the efficiency of the antenna. Some embodiments may overcome one or more previous limitations in ICP monitoring systems and wireless technologies by using miniaturized, battery-free implanted ICP sensors, such as can be manufactured by MEMS technology. Some embodiments may further employ biotelemetry, thereby allowing signal transmission in a fully passive manner rather than powering implanted electronics.

Embodiments may include subcutaneously embedded or surface-mounted fully-passive sensors that receive input electromagnetic signals from an external source and return one or more output electromagnetic signals, where these returned output electromagnetic signals may be used to determine pressure being applied to the embedded fully-passive sensor and/or the surface-mounted sensor. For example, a fully-passive sensor may be embedded in a location within the body, such as below the dura layer, subcranially, subcutaneously, on or within a bone, muscle, or organ, or elsewhere. The fully-passive sensor may remain there for subsequent reporting to a receiver, transceiver or other interrogator. Likewise, a surface-mounted, fully-passive sensor may be positioned on the dermis and remain there for testing. When an active input electromagnetic signal is received by the fully-passive sensor, the sensor may reflect a portion of the signal back (as described further below), and a receiver, transceiver or other interrogator may receive the reflected signal in order to determine pressure being applied to the fully-passive sensor or sensors. The portion of the signal reflected can generally be any portion. The wireless electromagnetic signal transmissions may be carried out across a layer of skin in some embodiments, with the sensor being embedded subcutaneously and the interrogator being outside the body, but other applications without an intervening layer of skin may also be employed.

Embodiments of embedded fully-passive sensors may be configured such that their impedance may be altered under different pressures. For example, when a sensor is under a first pressure, it may reflect a first output electromagnetic signal from a received input Pulse Width Modulation (PWM) signal; when the same sensor is under a second pressure, it may reflect back a second output electromagnetic signal from the same received input PWM signal. An interrogator may then determine, using the different input and output signals, what pressures and pressure changes are being experienced by the embedded fully-passive sensors.

In some embodiments, the reflected output electromagnetic signals may generally be any decibel in intensity. Examples of decibels include about $10^{-1}$, about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about $10^{-15}$ decibels. Given these low signal magnitudes, a receiver unit can be placed near the embedded sensor. The receiver unit can contain at least one receiver antenna for detecting the output electromagnetic signal. For example, the receiver unit can be placed in an article such as a helmet, clothing, shoe, bandage, pouch, pocket, band, or other area located outside of the body of a patient. The receiver unit may be located at any distance from the embedded sensor sufficient to read the output electromagnetic signal. For example, the receiver unit may be located within 20 mm of the embedded sensor. In some examples, the receiver unit may be within 13 mm-20 mm of an embedded sensor being activated and then read. In more specific examples, the receiving antennas may be within 13 mm, 14 mm, 15 mm, 16 mm, 17 mm, 18 mm, 19 mm, 20 mm, or any range between these values. Power levels for the output electromagnetic signals from the sensors may generally be any power. Examples of power levels include those on the order of $10^{-10}$ watts.

Embodiments may comprise a fully-passive pressure sensor that may include: a first substrate; a second substrate, a pressure sensor assembly mechanically coupled to the first substrate, the pressure sensor assembly comprising interdigitated electrical traces mounted on the second substrate; an antenna mechanically mounted to the first substrate; and a circuit mechanically coupled to the first substrate, wherein: the circuit is configured to receive an input electromagnetic signal via the antenna and to provide an output electromagnetic signal via the antenna, the output electromagnetic signal carrying information indicative of the amount of pressure being applied to the pressure sensor assembly, the second substrate is flexible, and the circuit does not contain a battery. In some examples, the fully-passive pressure sensor does not contain a battery.

As used herein, "flexible" refers to materials able to be bent or deflected by hand pressure at 37 degrees Celsius.

As used herein, the "pressure sensor assembly" contains one or more devices that allow a user to sense pressure (for example, one or more devices that change from one state to another when pressure is applied, as described herein).

The input electromagnetic signal may generally be any type of electromagnetic signal. The output electromagnetic signal may generally be any type of electromagnetic signal. The input electromagnetic signal and the output electromagnetic signal may be the same type or different types of electromagnetic signals. Exemplary types of electromagnetic signals (e.g., wave signals) are identified herein.

Embodiments may be further configured to provide a backscatter output electromagnetic signal upon receipt of the input electromagnetic signal, as well as potentially have interdigitated electrical traces that may be evenly spaced and positioned in a hollow of a pressure sensor assembly or other location. During operation, a circuit of certain embodiments may provide a responsive output electromagnetic signal through the antenna using power received from the received input electromagnetic signal. In some examples, the antenna may solely use power received from the received input electromagnetic signal. The received input electromagnetic signal may be a pulse-amplitude-modulated signal, pulse-duration-modulated signal, pulse-position-modulated signal, pulse-frequency-modulated signal, pulse-coded-modulated signal, pulse-width-modulated signal or any combination thereof. In some examples, the received input electromagnetic signal may be a pulse-width-modulated (PWM) signal. Also, in some embodiments, the substrates or other surfaces may be flexible. The first substrate and second substrate can have the same or different shape and size. The shape can be regular or irregular. Examples of regular shapes include square, circular, oval, rectangular, and so on. The size may generally be any size, such as having width or length independently of about 5 cm, about 4 cm, about 3 cm, about 2 cm, about 1 cm, about 0.5 cm, about 0.4 cm, about 0.3 cm, about 0.2 cm, about 0.1 cm, or ranges between any two of these values.

In some examples, the circuit may further comprise a varactor diode and an infrared activation photodiode. The varactor diode can be electrically coupled to the pressure sensor assembly, and the varactor diode can be electrically coupled to the infrared activation photodiode. In some examples, the interdigitated electrical traces may be evenly spaced.

A fully-passive pressure sensor system, in embodiments, may comprise a first flexible surface; a second surface; a first interdigitated electrode mechanically coupled to the first flexible surface, the first interdigitated electrode mounted between the first flexible surface and the second surface; a second interdigitated electrode mechanically coupled to the first flexible surface, the second interdigitated electrode mounted between the first flexible surface and the second surface; an antenna mechanically mounted to the first flexible surface, a circuit electrically coupled to the first interdigitated electrode and the second interdigitated electrode, the circuit configured to receive an input electromagnetic signal via the antenna and provide an output electromagnetic backscattered signal via the antenna, the output electromagnetic backscattered signal carrying information indicative of the amount of pressure being applied to the first flexible surface, the circuit not containing a battery; and at least one interrogator, the interrogator configured to receive the output electromagnetic backscattered signal and to calculate a force or pressure being received by the first flexible surface.

In embodiments, the interrogator is configured to direct the input electromagnetic signal to the antenna. In other embodiments, the circuit may further comprise a varactor diode and an infrared activation photodiode. The varactor diode is electrically coupled to the infrared activation photodiode. The varactor diode is electrically coupled to the first interdigitated electrode, the second interdigitated electrode, or both. In some embodiments, one or both of the first interdigitated electrode and second interdigitated electrode may be evenly spaced. In some embodiments, the first and second interdigitated electrodes may not be evenly spaced. In some embodiments, the first and second interdigitated electrodes may be positioned in a hollow between the first flexible surface and the second surface. The circuit may provide the output electromagnetic signal via the antenna partially or solely using power received from the input electromagnetic signal. In some embodiments, the received input electromagnetic signal may be a pulse-width-modulated signal.

The fully-passive pressure sensor systems described herein can be used to measure pressure in generally any system. The system can be a biological system or a non-biological system. A biological system can be any animal, including any mammal. Examples of mammals include a primate, a human, a dog, a cat, a mouse, a rat, a sheep, a cow, a horse, and a pig. The fully-passive pressure sensor system can be implanted to measure pressure within the biological system. The site of implantation can generally be any site.

A method of measuring subcutaneous pressure with a sensor system, in embodiments, may comprise providing an implanted sensor system comprising: a first substrate; a second flexible substrate, a pressure sensor assembly mechanically coupled to the first substrate, the pressure sensor assembly comprising interdigitated electrical traces mounted on the second flexible substrate; an antenna mechanically mounted to the first substrate; a circuit mechanically coupled to the first substrate, the circuit configured to receive an input electromagnetic wave via the antenna and provide an output electromagnetic signal via the antenna, the output electromagnetic signal carrying information indicative of the amount of pressure being applied to the pressure sensor assembly, wherein the circuit does not contain a battery; providing at least one interrogator, each interrogator configured to receive the output electromagnetic signal; delivering the input electromagnetic signal to the antenna; receiving the output electromagnetic signal via the interrogator; and calculating the subcutaneous pressure being received by the pressure sensor assembly.

In embodiments, the circuit may be configured to provide a backscatter output electromagnetic signal upon receipt of the input electromagnetic signal. The circuit may further comprise a varactor diode and an infrared activation photodiode. The varactor diode is electrically coupled to the pressure sensor assembly. The varactor diode is electrically coupled to the infrared activation photodiode. In some embodiments, the interdigitated electrical traces may be evenly spaced. The circuit may provide the output electromagnetic signal via the antenna partially or solely using power received from the received electromagnetic wave. In some embodiments, the received electromagnetic signal may be a pulse-width-modulated (PWM) signal. The first substrate may be flexible. The first substrate and second substrate can have the same or different shape and size. The shape can be regular or irregular. Examples of regular shapes include square, circular, oval, rectangular, and so on. The size may generally be any size, such as having width or length of about 5 cm, about 4 cm, about 3 cm, about 2 cm, about 1 cm, about 0.5 cm, about 0.4 cm, about 0.3 cm, about 0.2 cm, about 0.1 cm, or ranges between any two of these values.

FIG. 1 is a schematic illustration of an embodiment of a fully-passive pressure sensor system 100. A pressure value is determined using a pressure sensor assembly 120 on the fully-passive pressure sensor system 100. The measurement data are wirelessly transmitted to an external interrogator 200 (FIG. 4) in a completely passive, battery-free manner. The device may be fabricated from a wide variety of materials, such as copper clad polyimide with standard lithography and wet etching processes. Discrete surface-mount electronic components, including a photodiode 102, a varactor diode 104, resistors R1-R3 and capacitors C1-C2 (collectively 106), are soldered onto the first surface 108. One embodiment of the assembled fully-passive pressure sensor system 100 features a small footprint of about 9 mm×8 mm, and the height of the surface-mount components is about 0.85 mm, although it may be fabricated to other dimensions. In other embodiments of the assembled fully-passive pressure sensor system, the footprint may have a length and a width. The length may be, for example, from about 2 mm to about 30 mm; similarly, the width may be, for example, from about 2 mm to about 30 mm. The length and width may independently be, for example, about 2 mm, about 4 mm, about 2 mm, about 2 mm, about 2 mm, about 2 mm, about 2 mm, about 2 mm, about 2 mm, about 2 mm, about 2 mm, about 2 mm, about 2 mm, about 2 mm, or any range between any of these values. In some embodiments of the assembled fully-passive pressure sensor system, the height of the surface-mount components may be from about 0.2 mm to about 10 mm. The height may be, for example, about 0.2 mm, about 0.4 mm, about 0.6 mm, about 0.8 mm, about 1 mm, about 1.2 mm, about 1.4 mm, about 1.6 mm, about 1.8 mm, about 2 mm, about 2.2 mm, about 2.4 mm, about 2.6 mm, about 2.8 mm, about 3 mm, about 3.2 mm, about 3.4 mm, about 3.6 mm, about 3.8 mm, about 4 mm, about 4.2 mm, about 4.4 mm, about 4.6 mm, about 4.8 mm, about 5 mm, about 5.2 mm, about 5.4 mm, about 5.6 mm, about 5.8 mm, about 6 mm, about 6.2 mm, about 6.4 mm, about 6.6 mm, about 6.8 mm, about 7 mm, about 7.2 mm, about 7.4 mm, about 7.6 mm, about 7.8 mm, about 8 mm, about 8.2 mm, about 8.4 mm, about 8.6 mm, about 8.8 mm, about 9 mm, about 9.2 mm, about 9.4 mm, about 9.6 mm, about 9.8 mm, about 10 mm, or any range between these values.

Figure 2:
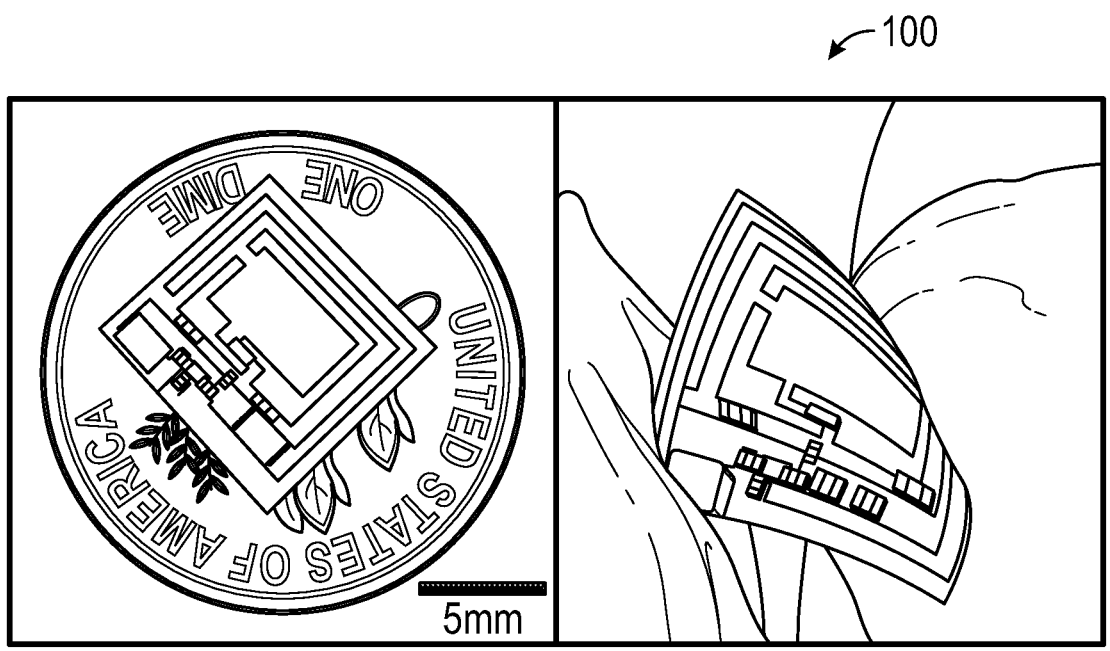
FIG. 2 illustrates an exemplary reference size for a fully-passive sensor system as may be employed in embodiments.

FIG. 2 is an example showing the possible scale of the fully-passive pressure sensor system 100. The fully-passive pressure sensor system 100 features a small footprint and high flexibility (demonstrated by the view on the right). In the view on the left, the fully-passive pressure sensor system 100 is shown on a reference object, a U.S. dime coin, to illustrate its relative size. The dime is 17.91 mm in diameter, and the fully-passive pressure sensor system is square in shape, having length and width of about 10 mm.

Figure 3:
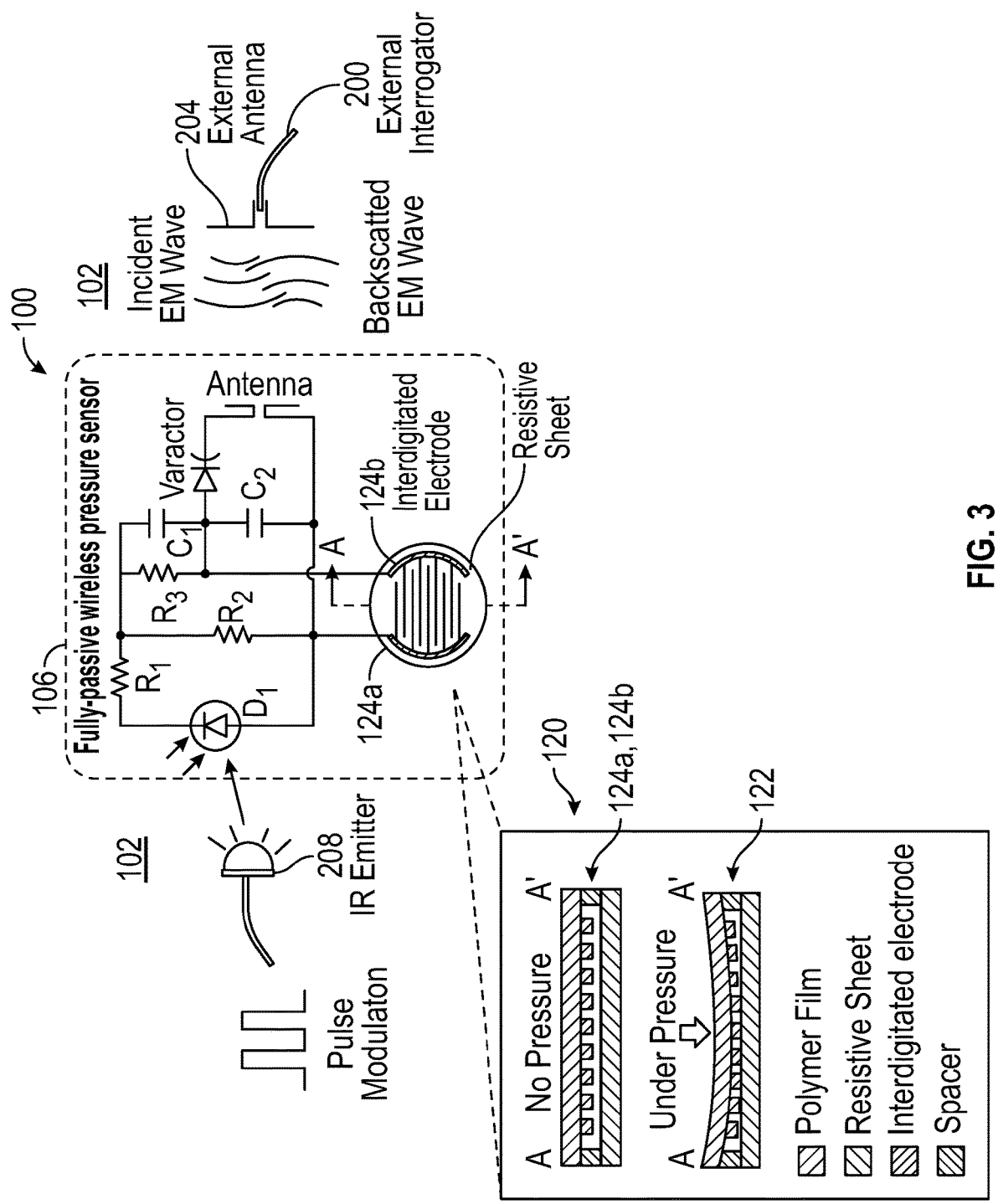
FIG. 3 illustrates a sensor system, including a cross-section of a fully-passive sensor under different loading conditions as may be employed in embodiments.

FIG. 3 is an example of a circuit of the fully-passive pressure sensor system 100 of FIG. 1 to illustrate the working principle of the fully-passive pressure sensor system 100. An external pulse on-off modulates the radiation of an infrared (IR) emitter 208, whose energy is subsequently detected and translated to a pulse wave signal by the photodiode (D1) 102 on the fully-passive pressure sensor system 100. The IR emitter 208 may be an IR light emitting diode (LED) emitter. The pressure sensor assembly 120 divides the generated pulse wave and outputs it to the varactor diode 104. An external interrogator 200 measures the voltage across the varactor diode 104 using an RF backscattering method through the antennae 110, 204.

Figure 4:
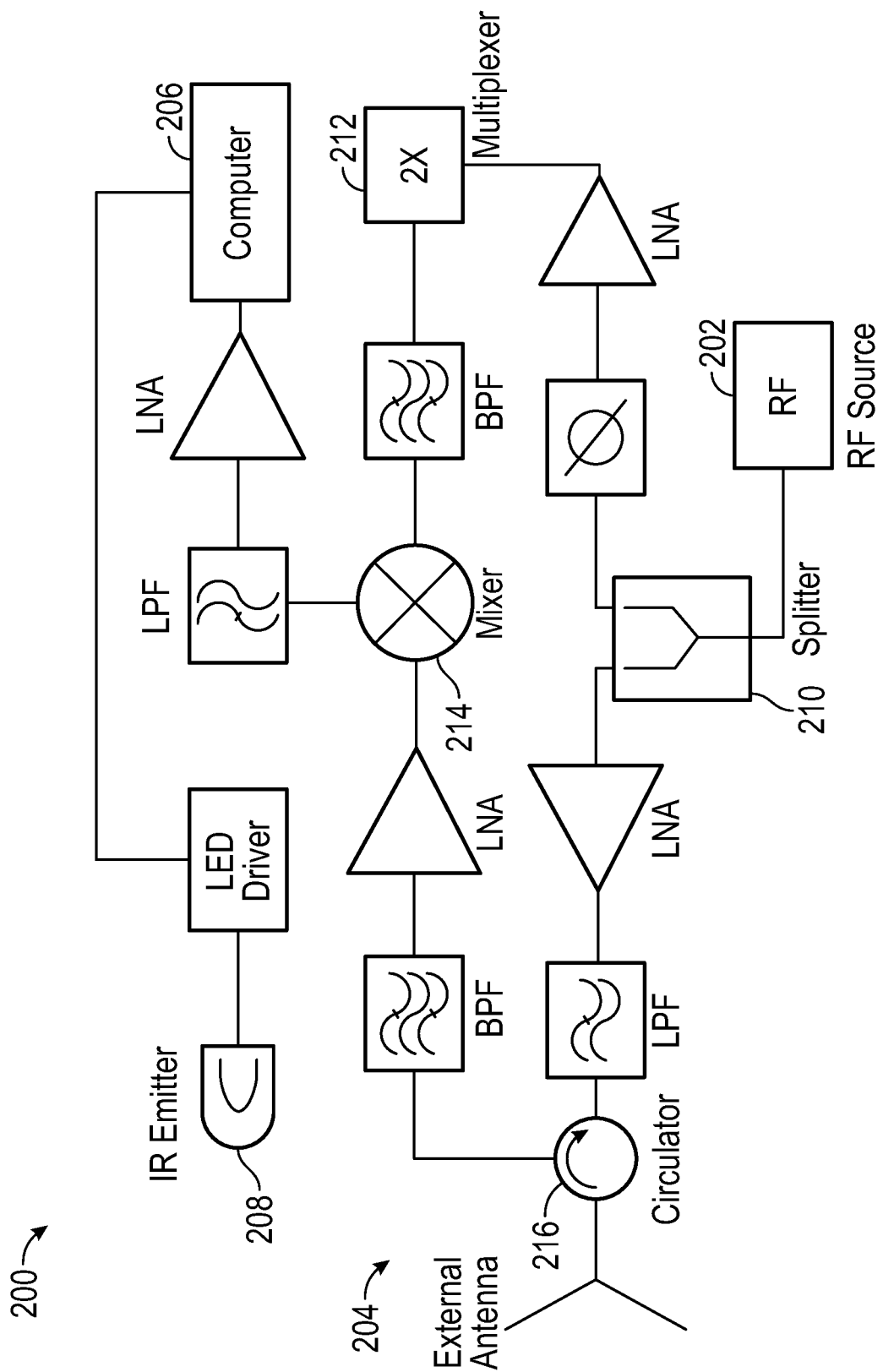
FIG. 4 illustrates a system topology of an external interrogator as may be employed in embodiments.

FIG. 4 is a block diagram of one embodiment of an external interrogator that may be used with the fully-passive pressure sensor system 100 of FIG. 3 and that employs the RF backscattering method. An RF source 202 produces a 2.4 GHz electromagnetic (EM) wave which is transmitted to the fully-passive pressure sensor system 100 through the external antenna 204. The fully-passive pressure sensor system 100 receives the input electromagnetic signal and reflects (backscatters) a modulated output electromagnetic signal back to the external antenna 204. The backscattered signal goes through a series of filtering and demodulation processes to extract the original voltage signal on the varactor diode 104. The obtained signal is sampled and processed by a computer 206 to calculate the target pressure value.

More specifically, to enable wireless acquisition of pressure, the pressure sensor assembly 120 first converts a pressure change into a resistance change using the contact between a finite conductive sheet 122 and the first and second interdigitated electrodes 124a, 124b (collectively 124). With the increase of pressure, the contact resistance between the finite conductive sheet 122 and the interdigitated electrodes 124 drops, decreasing the resistance between the interdigitated electrodes 124 as well. The resistance change between the first and second interdigitated electrodes 124 is converted into a variation of an electrical signal by the photodiode 102 (FIGS. 1, 3). The photodiode 102 receives infrared (IR) light from the external pulse modulated IR emitter 208, such as from the external interrogator 200, and transforms the light energy to an electrical voltage, producing a wave signal at its terminals. In some embodiments, the wave signal may be a square wave signal, a sine wave signal, a triangle wave signal, or a sawtooth wave signal. The wave signal produced may be a square wave. The wave signal is then voltage divided by the pressure sensor assembly 120 and applied to the varactor diode 104.

Embodiments may employ RF backscattering methods. For example, when the fully-passive pressure sensor system 100 receives an input electromagnetic signal whose frequency is $f_0$, the varactor diode 104 on the fully-passive pressure sensor system 100 mixes $f_0$ with any low frequency electrical signal ($f_m$) applied to its terminals. The mixing products ($2f_0 \pm f_m$) are then backscattered from the fully-passive pressure sensor system 100 and received by the external interrogator 200, which filters and demodulates the backscattered harmonic mixing products to extract the target signal ($f_m$).

With specific reference to embodiments, the RF source 202 of the external interrogator 200 (FIG. 4) may produce a sine wave RF signal which is divided into two parts through a power splitter 210. In one path, the RF signal ($f_0$) is amplified, filtered, and radiated through a dual band external antenna 204. In the second path, the signal goes through a multiplexer 212 to double the frequency and then is mixed with the backscattered third-order mixing products ($2f_0 \pm f_m$) from the fully-passive pressure sensor system 100 to down convert the target signal ($f_m$). A circulator 216 inserted at the output port of the external antenna 204 isolates backscattered signals ($2f_0 \pm f_m$) from the transmitting RF signals ($f_0$). The demodulated signal may be sampled using a data acquisition card, and may then be post-processed by the computer 206 to calculate the target pressure value. The sampling rate can generally be any suitable sampling rate.

As mentioned above, the resistance value between the two interdigitated electrodes 124 may be related to the external pressure value. Increasing the pressure can cause a decrease in the resistance. To read out the resistance change, R3, C1, and the pressure sensor assembly 120 form a voltage divider circuit, which divides the output voltage of the photodiode 102 based on the impedance ratio between R3‖C1 and the pressure sensor assembly 120. By way of a simplified example, the photodiode 102 presents a sine wave to the voltage divider circuit. The sine wave has a frequency of $f_1$ and amplitude of $A_{i1}$. The resistance of the fully-passive pressure sensor system 100 is $R_x$. Then the amplitude of output signal, $A_{o1}$ can be written as:

$$A_{o1} = \frac{R_x}{Z_{t1}} * A_{i1}$$

where $Z_{t1}$ represents the impedance of R3‖C1 (the impedance of R3 in parallel with C1). Suppose R3 is 100 KOhm and C1 is 1 nF, then $Z_{t1}$ can be expressed as:

$$Z_{t1} = \sqrt{10^{10}\left[\text{Im}\left(\frac{1}{1+i\frac{\pi f_1}{5000}}\right)\right]^2 + \left[R_x + 10^5 \text{Re}\left(\frac{1}{1+i\frac{\pi f_1}{5000}}\right)\right]^2}$$

where Re($f$) and Im($f$) denote the real and imaginary part off. The amplitude of voltage divider output signal, $A_{o1}$ is a function of the pressure sensor ($R_x$), the photodiode output voltage $A_{i1}$ and the modulation frequency $f_1$. The photodiode output voltage, $A_{i1}$, may be affected by the external environment, making the output, $A_{o1}$, unstable. To overcome such effect, a second modulation frequency $f_2$, is introduced. Under $f_2$, the output signal amplitude can be written as:

$$A_{o2} = \frac{R_x}{Z_{t2}} * A_{i2}$$

where $Z_{t2}$ is the impedance of R3‖C1 at $f_2$, which can be expressed as:

$$Z_{t2} = \sqrt{10^{10}\left[\text{Im}\left(\frac{1}{1+i\frac{\pi f_2}{5000}}\right)\right]^2 + \left[R_x + 10^5 \text{Re}\left(\frac{1}{1+i\frac{\pi f_2}{5000}}\right)\right]^2}$$

The ratio between $A_{o1}$ and $A_{o2}$ is:

$$\text{Ratio} = \frac{A_{o1}}{A_{o2}} = \frac{A_{i1} Z_{t2}}{A_{i2} Z_{t1}}$$

Because the voltage output by the diode detector is not affected by the frequency, $A_{i1} = A_{i2}$. Therefore, the ratio is:

$$\text{Ratio} = \frac{Z_{t2}}{Z_{t1}}$$

The above equation shows that the ratio is only a function of $R_x$, whose value is only related to the external pressure. To measure the pressure, the external interrogator 200 may be configured to modulate the IR LED emitter 208 using two frequencies ($f_1$ and $f_2$) alternatively, measure the amplitudes of backscattered signal, and calculate the ratio of amplitude to obtain the real time pressure value.

Figure 5:
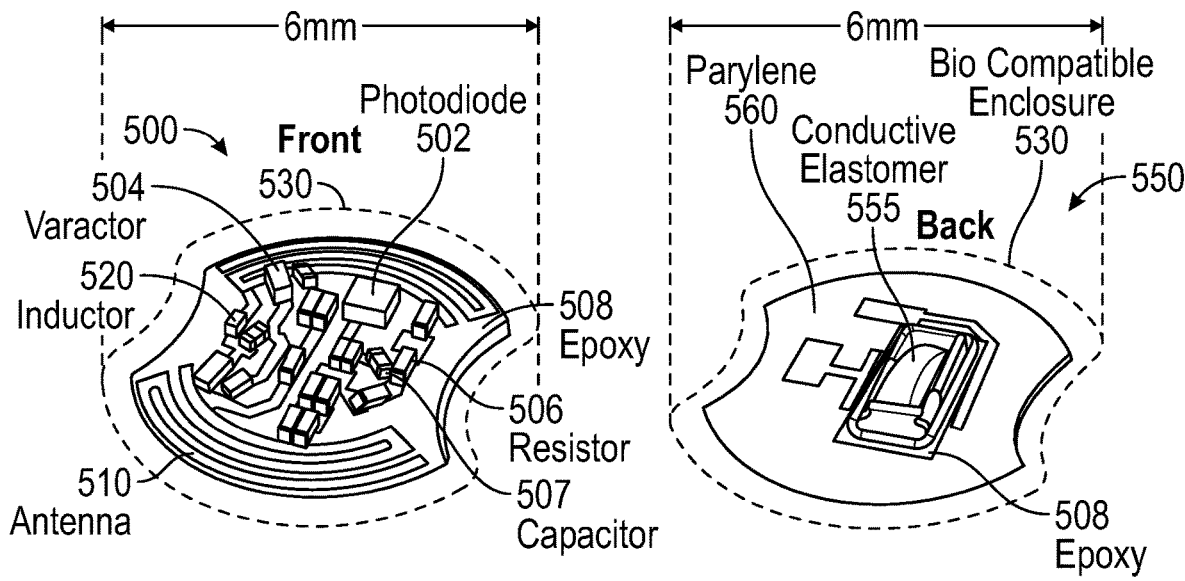
FIG. 5 illustrates front and back views of a fully-passive sensor system with biocompatible enclosure as may be employed in embodiments.

FIG. 5 shows front 500 and back 550 perspective views of a fully-passive pressure sensor system as may be employed in embodiments. The sensor in FIG. 5 is labeled with varactor 504, inductor 520, antenna 510, capacitor 507, resistor 506, epoxy 508, photodiode 502, biocompatible enclosure 530, conductive elastomer 555, and parylene 560. The epoxy 508 serves as a substrate for the various electronics of the sensor in FIG. 5. Scales for the front 500 and back 550 are also illustrated in FIG. 5 and show that the approximate diameter of the sensor, including the biocompatible enclosure, can be approximately 6 mm. Other sizes and shapes for the sensor are also possible. Moreover, the location of the electronics on the sensor may vary as well.

Figure 6:
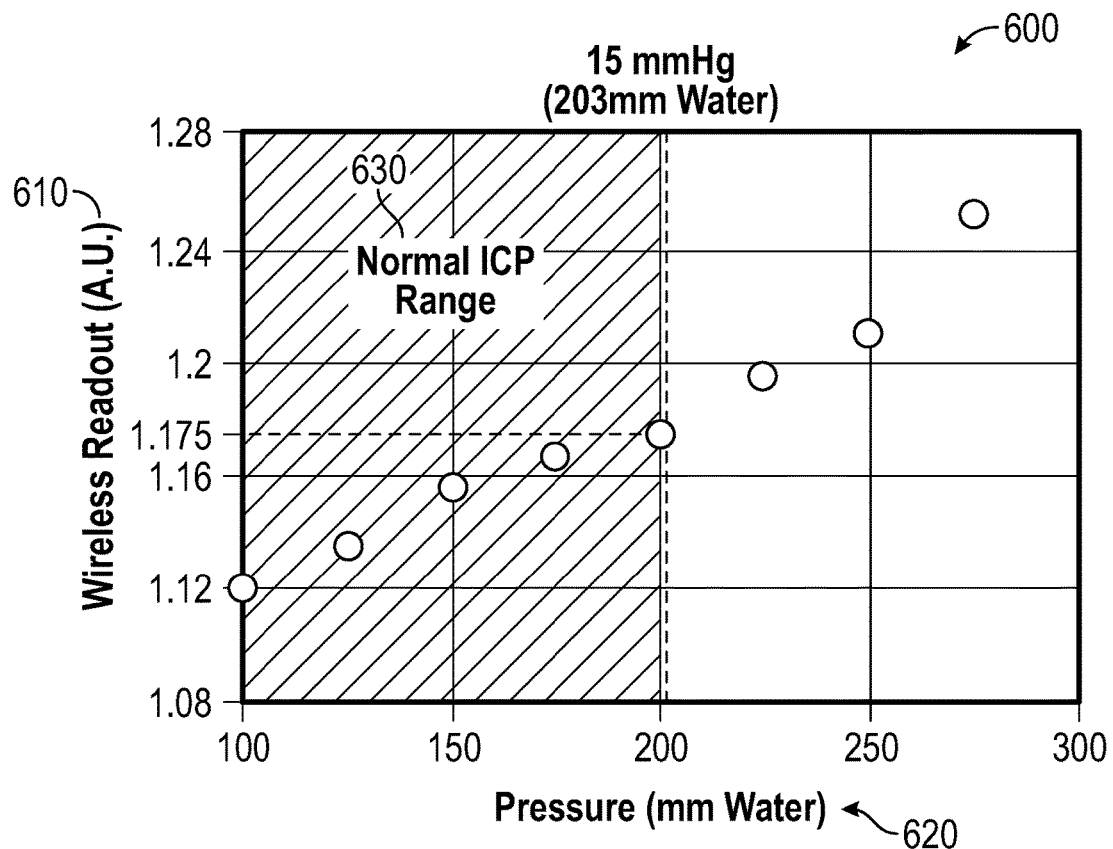
FIG. 6 illustrates exemplary sensor responses to increasing applied pressure as may be employed in embodiments.

FIG. 6 shows a graph with wireless outputs for exemplary fully-passive sensors of potential embodiments. This graph 600 shows applied pressure 620 in mm water along the x-axis and resulting wireless output 610 in A.U. along the y-axis. As shown, a somewhat increasing linear relationship between applied pressure and resulting wireless signal may be exhibited by sensor embodiments. For calibration purposes, sensors may be tested for wireless strength outputs at different applied pressures such that when outputs are received from a sensor, the outputs may be used to determine a previously unknown applied pressure at a target area of the body of a patient. A normal range 630 is also shown on graph 600. This normal range 630, which can be signified by receipt of signals at or below 1.175 micro-amps or other calibrated unit, can indicate that applied pressures at the target area are in an acceptable range. Comparatively, when received micro-amps or other wireless signal values exceed the normal wireless signal value, pressures may be considered to be exceeding this acceptable range. The acceptable range of pressure at a target area may depend on the various indications including the age of the patient, the patient's underlying health, the procedure being performed, and other factors as well.

While embodiments have been illustrated herein, it is not intended to restrict or limit the scope of the appended claims to such detail. In view of the teachings in this application, additional advantages and modifications will be readily apparent to and appreciated by those having ordinary skill in the art. Accordingly, changes may be made to the above embodiments. Various features, steps, processes, components, and subcomponents may be employed in certain embodiments. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure unless otherwise indicated herein or otherwise clearly contradicted by context. All methods described herein can be performed in any suitable order unless otherwise indicated herein or otherwise clearly contradicted by context.

The terminology used herein is for the purpose of describing particular embodiments only and is not intended to be limiting. As used herein, the singular forms "a," "an" and "the" are intended to include plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The use of any and all examples, or exemplary language (for example, "such as") provided herein, is intended merely to better illuminate and does not pose a limitation on scope unless otherwise claimed. No language in the specification should be construed as indicating any non-claimed element as essential.

As used herein, the terms "about" or "approximately" in reference to a recited numeric value, including for example, whole numbers, fractions, and/or percentages, generally indicates that the recited numeric value encompasses a range of numerical values (for example, ±5% to 10% of the recited value) that one of ordinary skill in the art would consider equivalent to the recited value (for example, performing substantially the same function, acting in substantially the same way, and/or having substantially the same result).

Recitation of ranges of values herein are merely intended to serve as a shorthand method of referring individually to each separate value falling within the range, unless otherwise indicated herein, and each separate value is incorporated into the specification as if it were individually recited herein.

It should be noted that the terms "first", "second", and "third", and the like may be used herein to modify elements performing similar and/or analogous functions. These modifiers do not imply a spatial, sequential, or hierarchical order to the modified elements unless specifically stated.

Certain embodiments may be implemented as a computer process, a computing system or as an article of manufacture such as a computer program product of computer readable media. The computer program product may be a computer storage medium readable by a computer system and encoding computer program instructions for executing a computer process.

The corresponding structures, material, acts, and equivalents of any means or steps plus function elements in the claims are intended to include any structure, material or act for performing the function in combination with other claimed elements. The description of certain embodiments has been presented for purposes of illustration and description, but is not intended to be exhaustive or limited in the form disclosed. Many modifications and variations will be apparent to those of ordinary skill without departing from the scope and spirit. These embodiments were chosen and described in order to best explain certain principles and the practical application, and to enable others of ordinary skill in the art to understand embodiments and that various modifications are suitable.

What is claimed is:

1. A fully-passive pressure sensor system, comprising: a first substrate;
    a second substrate;
    a pressure sensor assembly mechanically coupled to the first substrate, the pressure sensor assembly comprising interdigitated electrical traces mounted on the second substrate;
    an antenna mechanically mounted to the first substrate; and a circuit mechanically coupled to the first substrate, wherein:
    the circuit is configured to receive an input electromagnetic signal via the antenna; the circuit is configured to provide an output electromagnetic signal via the antenna; the output electromagnetic signal carrying information indicative of the amount of pressure being applied to the pressure sensor assembly; the second substrate is flexible; and the circuit does not contain a battery; and wherein the circuit further comprises a varactor diode and an infrared activation photodiode; the varactor diode is electrically coupled to the pressure sensor assembly; and the varactor diode is electrically coupled to the infrared activation photodiode.

2. The pressure sensor system of claim 1, wherein the output electromagnetic signal is a backscatter electromagnetic signal.

3. The pressure sensor system of claim 1, wherein the interdigitated electrical traces are evenly spaced.

4. The pressure sensor system of claim 1, wherein the circuit is configured to provide the output electromagnetic signal through the antenna using power received from the input electromagnetic signal.

5. The pressure sensor system of claim 1, wherein the input electromagnetic signal is a pulse-width-modulated (PWM) signal.

6. The pressure sensor system of claim 1, wherein the first substrate is flexible.

7. A fully-passive pressure sensor system comprising: a first flexible surface;
a second surface;
a first interdigitated electrode mechanically coupled to the first flexible surface, the first interdigitated electrode mounted between the first flexible surface and the second surface;
a second interdigitated electrode mechanically coupled to the first flexible surface, the second interdigitated electrode mounted between the first flexible surface and the second surface;
an antenna mechanically mounted to the first flexible surface;
a circuit electrically coupled to the first interdigitated electrode and the second interdigitated electrode, the circuit configured to receive an input electromagnetic signal via the antenna and provide an output electromagnetic backscattered signal via the antenna, the output electromagnetic backscattered signal carrying information indicative of the amount of pressure being applied to the first flexible surface, wherein the circuit does not contain a battery; wherein the circuit further comprises a varactor diode and an infrared activation photodiode; the varactor diode is electrically coupled to the infrared activation photodiode; and the varactor diode is electrically coupled to the first interdigitated electrode, the second interdigitated electrode, or both; and
at least one interrogator, the interrogator configured to receive the output electromagnetic backscattered signal and calculate a force or pressure being received by the first flexible surface.

8. The pressure sensor system of claim 7, wherein the interrogator is configured to direct the input electromagnetic signal to the antenna.

9. The pressure sensor system of claim 7, wherein the first interdigitated electrode and the second interdigitated electrode are evenly spaced.

10. The pressure sensor system of claim 7, wherein the circuit provides the output electromagnetic signal through the antenna using power received from the input electromagnetic signal.

11. The pressure sensor of claim 7, wherein the input electromagnetic signal is a pulse-width-modulated signal.

12. A method of measuring subcutaneous pressure, the method comprising: providing an implanted sensor system comprising:
a first substrate;
a second flexible substrate;
a pressure sensor assembly mechanically coupled to the first substrate, the pressure sensor assembly comprising interdigitated electrical traces mounted on the second flexible substrate;
an antenna mechanically mounted to the first substrate;
a circuit mechanically coupled to the first substrate, the circuit configured to receive an input electromagnetic signal via the antenna and to provide an output electromagnetic signal through the antenna, the output electromagnetic signal carrying information indicative of the amount of pressure being applied to the pressure sensor assembly; wherein the circuit does not contain a battery; wherein the circuit further comprises a varactor diode and an infrared activation photodiode; wherein the varactor diode is electrically coupled to the pressure sensor assembly; and the varactor diode is electrically coupled to the infrared activation photodiode;
providing at least one interrogator configured to receive the output electromagnetic signal;
delivering the input electromagnetic signal to the antenna;
receiving the output electromagnetic signal via the interrogator; and
calculating the subcutaneous pressure received by the pressure sensor assembly.

13. The method of claim 12, wherein the output electromagnetic signal is a backscatter electromagnetic signal.

14. The method of claim 12, wherein the interdigitated electrical traces are evenly spaced.

15. The method of claim 12, wherein the circuit is configured to provide the output electromagnetic signal through the antenna using power received from the input electromagnetic signal.

16. The method of claim 12, wherein the input electromagnetic signal is a pulse-width-modulated (PWM) signal.

17. The method of claim 12, wherein the first substrate is flexible.

* * * * *